(12) United States Patent
Shi

(10) Patent No.: US 9,249,106 B2
(45) Date of Patent: Feb. 2, 2016

(54) SUBSTITUTED HYDRAZIDE COMPOUNDS AND USE THEREOF

(75) Inventor: Xiulan Shi, Xinmin (CN)

(73) Assignee: Shenyang J & Health Pharmaceutical Co., Ltd., Xinmin, Liaoning (CN)

( * ) Notice: Subject to any disclaimer, the term of this patent is extended or adjusted under 35 U.S.C. 154(b) by 0 days.

(21) Appl. No.: 13/390,657

(22) PCT Filed: Aug. 9, 2010

(86) PCT No.: PCT/CN2010/001209
§ 371 (c)(1),
(2), (4) Date: Feb. 15, 2012

(87) PCT Pub. No.: WO2011/020288
PCT Pub. Date: Feb. 24, 2011

(65) Prior Publication Data
US 2012/0142921 A1 Jun. 7, 2012

(30) Foreign Application Priority Data
Aug. 19, 2009 (CN) .......................... 2009 1 0163003

(51) Int. Cl.
| | | |
|---|---|---|
| C07D 235/06 | (2006.01) | |
| C07D 405/12 | (2006.01) | |
| C07D 401/04 | (2006.01) | |
| C07D 417/14 | (2006.01) | |
| C07D 403/12 | (2006.01) | |
| C07D 235/16 | (2006.01) | |
| A61K 9/00 | (2006.01) | |
| A61K 47/10 | (2006.01) | |

(52) U.S. Cl.
CPC ............ *C07D 235/06* (2013.01); *C07D 235/16* (2013.01); *C07D 401/04* (2013.01); *C07D 403/12* (2013.01); *C07D 405/12* (2013.01); *C07D 417/14* (2013.01); *A61K 9/0014* (2013.01); *A61K 9/0019* (2013.01); *A61K 9/0031* (2013.01); *A61K 9/0078* (2013.01); *A61K 47/10* (2013.01)

(58) Field of Classification Search
CPC ...... C09B 57/04; C09B 23/10; C09B 23/107; C09B 23/105; C09B 23/04
See application file for complete search history.

(56) References Cited

U.S. PATENT DOCUMENTS

2008/0300240 A1   12/2008   Bergmann et al.

FOREIGN PATENT DOCUMENTS

| CN | 87104648 A | 4/1988 |
|---|---|---|
| CN | 101624376 A | 1/2010 |
| EP | 1 361 224 A1 | 11/2003 |
| WO | 2008/064342 A2 | 5/2008 |
| WO | WO 2008064342 A2 * | 5/2008 |

OTHER PUBLICATIONS

International Search Report, mailed Dec. 16, 2010, for PCT/CN2010/001209, 4 Pages.
Written Opinion, mailed Dec. 16, 2010, for PCT/CN2010/001209, 6 Pages.
Chem Abstract No. 69:86771 & Cemischev et al. "Synthesis of some potential tuberculostatics: hydrazides and hydrazones of 2-, 3-, and 4-pyridylacetic acids, o-, m-, and p-cyanobenzoic acids, and 2-benzimidazolylacetic acid," *Pharmazie* 22(8):432-4, 1967, 3 Pages.
Chem Abstract No. 138:24453 & K. I. Kobrakov et al. "Synthesis of diheteroaryl-substituted hydrazones and N-acylhydrazones," *Bashkirskii Khimischeskii Zhurnal* 8(4):3-9, 2001, 2 Pages.
Galal et al. "New transition metal ion complexes with benzimidazole-5-carboxylic acid hydrazides with antitumor activity," *European Journal of Medicinal Chemistry* 44:1500-8, 2009.
Graubaum et al. "About the reactions of benzimidazole-2-carbohydrazide with electrophilic compounds," *Journal fuer Praktische Chemie* 328(4):515-21, 1986.
Shukla et al. "Substituted benzimidazoles as possible antitubercular compounds," *Journal fuer Praktische Chemie* 311(1):187-9, 1969.
Cemischev, B. and Popov, D. 1967 "For the synthesis of some potential Tuberculostatica hydrazide and hydrazones of 2-, 3- and 4-pyridyl acetic acid, o-, m- and p-Cyanbenzoesaure and 2-Benzimidazoylessigsaure" *Pharmazie* 22(8): 432-434.
Galal, S.A. et al. 2008 "New transition metal ion complexes with benzimidaz1oe-5-carboxylic acid hydrazides with antitumor activity" *Eur J Med Chem* 44: 1500-1508.
Graubaum H. and Martin D. 1986 "About the reactions of Benzimidazole-2-carbohydrazide with electrophilic compounds" *J Prakt Chemio* 328: 515-521.
Office Action in corresponding Japanese Application No. JP 2012-525021, dated Aug. 27, 2013.
Shukla, J.S. et al. 1969 "Substituted benzimidazoles as possible antitubercular compounds" *J Prakt Chemio* 311: 187-189.
Second Japanese Office Action in Japanese Application No. 2012-525021 dated Jun. 3, 2014 in 3 pages.
Hall, I.H. et al. 1999 "Investigations on the mechanism of action of the novel antitumor agents 2-Benzothiazolyl, 2-Benzoxazoylyl, and 2-Benzimidazolyl hydrazones derived from 2-Acetylpyridine" *Arch Pharm Pharm Med Chem* 332: 115-123.
Office Action in corresponding Canadian Application No. 2,771,234, dated Dec. 3, 2013.
Supplemental European Search Report in corresponding European Application No. EP 10 80 9422, dated Jan. 31, 2014.

* cited by examiner

Primary Examiner — San-Ming Hui
Assistant Examiner — Andrew Lee
(74) *Attorney, Agent, or Firm* — Knobbe, Martens, Olson & Bear, LLP

(57) ABSTRACT

The invention relates to substituted hydrazide compounds as shown by general formula I, including geometrical isomers, pharmaceutically acceptable salts, hydrates, solvates or prodrugs thereof, and use of the same, wherein the substitutents Ar and R have the same meanings as given in the Description. The invention further relates to the use of compounds of general formula I in the preparation of medicament for the treatment and/or prevention of cancer and other proliferative diseases.

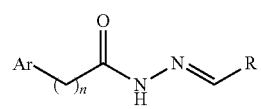

3 Claims, No Drawings

SUBSTITUTED HYDRAZIDE COMPOUNDS AND USE THEREOF

FIELD OF THE INVENTION

The present invention belongs to the field of medicament technology, and relates to the novel substituted hydrazide compounds, the geometrical isomers, pharmaceutically acceptable salts, hydrates, solvates or prodrug thereof, and the preparation method thereof as well as a pharmaceutical composition comprising the same. The present invention further relates to the uses of the derivatives for the preparation of medicaments for the treatment and/or prevention of cancer and other proliferative diseases.

BACKGROUND OF THE INVENTION

Cancer is a disease seriously threatening human life. According to the statistics of WHO in 2008, people died of cancer in 2007 amounts to 7.9 million, which represents about 13% of all death tolls. Recently, with a deeper study into the tumorigenesis mechanism, the molecular mechanisms involving in the genesis and development of cancer are revealed gradually, and anti-tumor drugs have developed from initial cytotoxic drugs into tumor-specific targeted drugs.

Cell death can be divided into necrosis and programmed cell death, of which the most important type is apoptosis. Recent studies have revealed that the tumorigenesis and progression are resulted from not only uncontrolled cell proliferation and abnormal differentiation, but also imbalance of apoptosis. Apoptosis is a cell active death progress under the control of related genes which is triggered by a change of insider and outside environments or death signal, and can eliminate aged cells and potentially abnormal growing cells in vivo under physiological conditions. Therefore, it plays an important role in maintaining homeostasis in vivo. With a deeper study into the mechanism of apoptosis, many proteins have been identified to involve in apoptosis, including IAP family proteins, Smac/DIABLO protein, Bcl-2 family proteins, P53 gene, Proteasome proteinase, Caspase family proteins and so on.

Chemistry Professor Paul J. Hergenrother et al. at the University of Illinois found a small molecule compound PAC-1 by screening more than 20000 compounds with different structures. PAC-1 could activate Procaspase-3 directly and induce the apoptosis of cancer cells. Studies showed that PAC-1 could activate Procaspase-3 significantly both in vitro and in vivo, and cancer cells would be also induced to apoptosis within 23 hours after treatment with PAC-1.

PAC-1

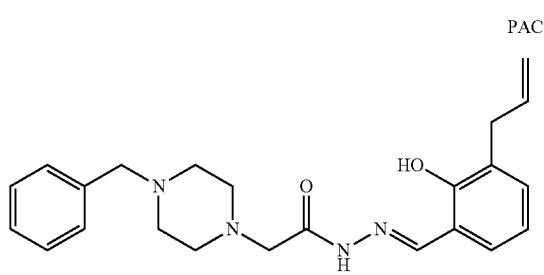

Based on the references, the inventor designs and synthesizes a serial of substituted hydrazide compounds, which are shown to possess a strong antitumor activity and little side effect by in vitro screening assay for antitumor activity on various tumor cell strains.

SUMMARY OF THE INVENTION

The invention relates to substituted hydrazide compounds of formula I, or geometrical isomers or pharmaceutically acceptable salts or hydrates or solvates or prodrug thereof,

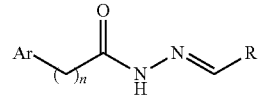

I wherein
Ar is a 5 to 10 membered heteroaryl group, which contains 1 to 3 heteroatoms selected from O, N and S, and Ar is optionally substituted with 1 to 3 same or different $R_1$;

$R_1$ is hydrogen, hydroxyl, halogen, trifluoromethyl, trifluoromethoxy, carboxyl, amino, triazo, nitro, cyano, sulfhydryl, aryl, aryl($C_1$-$C_4$)alkyl, aryl($C_1$-$C_4$)alkoxyl, $C_3$-$C_6$ cycloalkyl, $C_3$-$C_6$ cycloalkyl $C_1$-$C_4$ alkyl, 5 to 10 membered heteroaryl, 5 to 10 membered heteroaryl($C_1$-$C_4$)alkyl, 5 to 10 membered saturated or partially saturated heterocyclic group, or 5 to 10 membered saturated or partially saturated heterocyclic group $C_1$-$C_4$ alkyl, wherein said heteroaryl and heterocyclic group contain 1 to 3 heteroatoms selected from O, N and S;

R is phenyl, naphthyl, 5 to 10 membered heteroaryl, or 5 to 10 membered saturated or partially saturated heterocyclic group, wherein said heteroaryl and heterocyclic group contain 1 to 3 heteroatoms selected from O, N and S, and R is optionally substituted with 1 to 4 same or different $R_2$;

$R_2$ is hydrogen, hydroxyl, halogen, trifluoromethyl, trifluoromethoxy, carboxyl, amino, triazo, nitro, cyano, sulfhydryl, ($C_1$-$C_4$)alkyl, ($C_1$-$C_4$)alkenyl, ($C_1$-$C_4$)alkynyl, ($C_1$-$C_4$)alkoxyl, ($C_1$-$C_4$)alkylthio, hydroxy($C_1$-$C_4$)alkyl, amino ($C_1$-$C_4$)alkyl, allyl, (2-methyl)allyl, (3-methyl)allyl, (2-methyl)-2-butenyl, ($C_1$-$C_4$)alkylamido, ($C_1$-$C_4$)alkylsulfinyl, ($C_1$-$C_4$)alkylsulfonyl, ($C_1$-$C_4$)alkoxylmethyl, ($C_1$-$C_4$)alkylacyl, aminoformyl, N—($C_1$-$C_4$)alkylaminoformyl, N,N-di($C_1$-$C_4$)alkylaminoformyl, aminosulfonyl, N—($C_1$-$C_4$)alkylaminosulfonyl, N,N-di($C_1$-$C_4$)alkylaminosulfonyl, ($C_1$-$C_3$)alkylenedioxy, chloroacetyl, arylmethoxy, or 5-10 membered heteroarylmethoxy, wherein said heteroaryl contains 1 to 3 heteroatoms selected from O, N and S, and the aryl or heteroaryl may be optionally substituted with 1 to 3 $R_3$;

$R_3$ is hydrogen, hydroxyl, halogen, trifluoromethyl, trifluoromethoxy, carboxyl, amino, triazo, nitro, cyano, sulfhydryl, ($C_1$-$C_4$)alkyl, ($C_1$-$C_4$)alkenyl, ($C_1$-$C_4$)alkynyl, ($C_1$-$C_4$)alkoxyl, arylmethoxy, or benzo[1,3]-dioxolan-5-yl-methyl; and n is an integer between 0 and 4;
provided that:
when Ar is

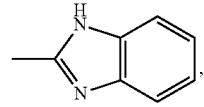

, n=1, R₁ is hydrogen, and R is phenyl, then R₂ is not 2,4-dimethoxy or 3,4-dimethoxy;

when Ar is

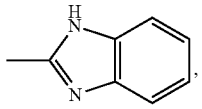

n=1, R₁ is hydrogen, and R is furan-2-yl, then R₂ is not nitro;

when Ar is

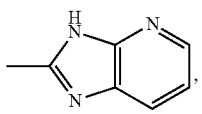

n=1, R₁ is hydrogen, and R is phenyl, then R₂ is not hydrogen.

Preferably, the present invention relates to a compound of general formula I, the geometrical isomers, pharmaceutically acceptable salts, hydrates, solvates or prodrug thereof, wherein, Ar is a 5 to 10 membered heteroaryl group, which contains 1 to 3 heteroatoms selected from O, N and S, and Ar is optionally substituted with 1 to 3 same or different $R_1$;

$R_1$ is hydrogen, aryl($C_1$-$C_4$)alkoxyl, 5 to 10 membered heteroaryl, or 5 to 10 membered heteroaryl($C_1$-$C_4$)alkyl, wherein said heteroaryl group contains 1 to 3 heteroatoms selected from O, N and S;

R is phenyl, naphthyl, 5 to 10 membered heteroaryl, or 5 to 10 membered saturated or partially saturated heterocyclic group, wherein said heteroaryl and heterocyclic group contain 1 to 3 heteroatoms selected from O, N and S, and R is optionally substituted with 1 to 4 same or different $R_2$;

$R_2$ is hydrogen, hydroxyl, halogen, trifluoromethyl, trifluoromethoxy, carboxyl, amino, triazo, nitro, cyano, sulfhydryl, ($C_1$-$C_4$)alkyl, ($C_1$-$C_4$)alkenyl, ($C_1$-$C_4$)alkynyl, ($C_1$-$C_4$)alkoxyl, ($C_1$-$C_4$)alkylthio, hydroxy($C_1$-$C_4$)alkyl, amino ($C_1$-$C_4$)alkyl, allyl, (2-methyl)allyl, (3-methyl)allyl, (2-methyl)-2-butenyl, ($C_1$-$C_4$)alkylamido, ($C_1$-$C_4$)alkylsulfinyl, ($C_1$-$C_4$)alkylsulfonyl, ($C_1$-$C_4$)alkoxylmethyl, ($C_1$-$C_4$)alkylacyl, aminoformyl, N—($C_1$-$C_4$)alkylaminoformyl, N,N-di($C_1$-$C_4$)alkylaminoformyl, aminosulfonyl, N—($C_1$-$C_4$)alkylaminosulfonyl, N,N-di($C_1$-$C_4$)alkylaminosulfonyl, ($C_1$-$C_3$)alkylenedioxy, chloroacetyl, arylmethoxy, or 5-10 membered heteroarylmethoxy, wherein said heteroaryl contains 1 to 3 heteroatoms selected from O, N and S, and the aryl or heteroaryl may be optionally substituted with 1 to 3 $R_3$;

$R_3$ is hydrogen, hydroxyl, halogen, trifluoromethyl, trifluoromethoxy, carboxyl, amino, triazo, nitro, cyano, sulfhydryl, ($C_1$-$C_4$)alkyl, ($C_1$-$C_4$)alkenyl, ($C_1$-$C_4$)alkynyl, ($C_1$-$C_4$)alkoxyl, arylmethoxy, or benzo[1,3]-dioxolan-5-yl-methyl; and n is 0 or 1.

More preferably, the present invention relates to a compound of general formula I, the geometrical isomers, pharmaceutically acceptable salts, hydrates, solvates or prodrug thereof, wherein,

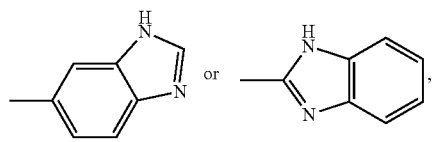

and Ar is optionally substituted with 1 to 3 same or different $R_1$;

$R_1$ is hydrogen, aryl $C_1$-$C_4$ alkoxyl, or 5 to 10 membered heteroaryl, wherein said heteroaryl group contains 1 to 3 heteroatoms selected from O, N and S;

R is phenyl, naphthyl, or pyrimidinetrione, and R is optionally substituted with 1 to 4 same or different $R_2$;

$R_2$ is hydrogen, hydroxyl, halogen, trifluoromethyl, trifluoromethoxy, carboxyl, amino, triazo, nitro, cyano, sulfhydryl, ($C_1$-$C_4$)alkyl, ($C_1$-$C_4$)alkenyl, ($C_1$-$C_4$)alkynyl, ($C_1$-$C_4$)alkoxyl, ($C_1$-$C_4$)alkylthio, hydroxy($C_1$-$C_4$)alkyl, amino ($C_1$-$C_4$)alkyl, allyl, (2-methyl)allyl, (3-methyl)allyl, (2-methyl)-2-butenyl, ($C_1$-$C_4$)alkylamido, ($C_1$-$C_4$)alkylsulfinyl, ($C_1$-$C_4$)alkylsulfonyl, ($C_1$-$C_4$)alkoxylmethyl, ($C_1$-$C_4$)alkylacyl, aminoformyl, N—($C_1$-$C_4$)alkylaminoformyl, N,N-di($C_1$-$C_4$)alkylaminoformyl, amino sulfonyl, N—($C_1$-$C_4$)alkylaminosulfonyl, N,N-di($C_1$-$C_4$)alkylaminosulfonyl, ($C_1$-$C_3$)alkylenedioxy, chloroacetyl, arylmethoxy, or 5-10 membered heteroarylmethoxy, wherein said heteroaryl contains 1 to 3 heteroatoms selected from O, N and S, and the aryl or heteroaryl may be optionally substituted with 1 to 3 $R_3$;

$R_3$ is hydrogen, hydroxyl, halogen, trifluoromethyl, trifluoromethoxy, carboxyl, amino, triazo, nitro, cyano, sulfhydryl, (C₁-C₄)alkyl, (C₁-C₄)alkenyl, (C₁-C₄)alkynyl, (C₁-C₄) alkoxyl, arylmethoxy, or benzo[1,3]-dioxolan-5-yl-methyl; and n is 0 or 1.

Especially preferably, the present invention relates to a compound of general formula I, the geometrical isomers, pharmaceutically acceptable salts, hydrates, solvates or prodrug thereof, wherein,

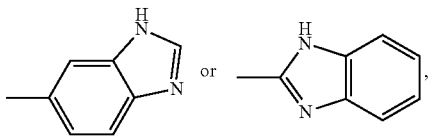

and Ar is optionally substituted with 1 to 3 same or different R₁;

R₁ is hydrogen, benzyloxy, or pyridine-4-yl;

R is phenyl, naphthyl, or pyrimidinetrione, and R is optionally substituted with 1 to 4 same or different R₂;

R₂ is hydrogen, hydroxyl, halogen, trifluoromethyl, trifluoromethoxy, cyano, (C₁-C₄)alkyl, (C₁-C₄)alkenyl, (C₁-C₄) alkoxyl, allyl, (2-methyl)allyl, (3-methyl)allyl, (2-methyl)-2-butenyl, (C₁-C₄)alkylacyl, (C₁-C₃)alkylenedioxy, chloroacetyl, arylmethoxy, or 5-10 membered heteroarylmethoxy, wherein said heteroaryl contains 1 to 3 heteroatoms selected from O, N and S, and the aryl or heteroaryl may be optionally substituted with 1 to 3 R₃;

R₃ is hydrogen, halogen, or benzo[1,3]-dioxolan-5-yl-methyl; and n is 0 or 1.

Most preferably, the present invention relates to a compound of general formula I, the geometrical isomers, pharmaceutically acceptable salts, hydrates, solvates or prodrug thereof, wherein,

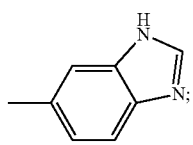

R is phenyl, and R is optionally substituted with 1 to 4 same or different R₂;

R₂ is hydrogen, hydroxyl, halogen, trifluoromethyl, trifluoromethoxy, cyano, (C₁-C₄)alkyl, (C₁-C₄)alkenyl, (C₁-C₄) alkoxyl, allyl, (2-methyl)allyl, (3-methyl)allyl, (2-methyl)-2-butenyl, (C₁-C₄)alkylacyl, (C₁-C₃)alkylenedioxy, chloroacetyl, arylmethoxy, or 5-10 membered heteroarylmethoxy, wherein said heteroaryl contains 1 to 3 heteroatoms selected from O, N and S, and the aryl or heteroaryl may be optionally substituted with 1 to 3 R₃;

R₃ is hydrogen, or halo; and n is 0.

The most preferable particular compounds of instant invention are as follows:

N'-[(2-hydroxy-3,5-di-tert-butyl)phenylmethylene]-1H-benzo[d]imidazole-6-formhydrazide N'-[(2-hydroxy-3-allyl)phenylmethylene]-1H-benzo[d]imidazole-6-formhydrazide N'-[(2-hydroxy-4-methyl)phenylmethylene]-1H-benzo[d]imidazole-6-formhydrazide N'-[(2-hydroxy-1-naphthyl)methylene]-1H-benzo[d]imidazole-6-formhydrazide N'-{2-hydroxy-4-[2-(3,4-dioxomethylenebenzyl)thiazol-4-yl-methoxy]phenylmethylene}-1H-benzo[d]imidazole-6-formhydrazide N'-[(2-hydroxy-3,4,6-trimethyl)phenylmethylene]-1H-benzo[d]imidazole-6-formhydrazide N'-[(2-hydroxy-5-methyl)phenylmethylene]-1H-benzo[d]imidazole-6-formhydrazide N'-[(2-hydroxy-3-methyl-6-isopropyl)phenylmethylene]-1H-benzo[d]imidazole-6-formhydrazide N'-[(2-hydroxy-5-chloroacetyl)phenylmethylene]-1H-benzo[d]imidazole-2-acethydrazide N'-[(2-hydroxy-3,4,6-trimethyl)phenylmethylene]-1H-benzo[d]imidazole-2-acethydrazide N'-[(2-hydroxy-4-methyl)phenylmethylene]-1H-benzo[d]imidazole-2-acethydrazide N'-[(2-hydroxy-5-benzyloxy)phenylmethylene]-1H-benzo[d]imidazole-2-acethydrazide N'-[(2-hydroxy-3,5-di-tert-butyl)phenylmethylene]-1H-benzo[d]imidazole-2-acethydrazide N'-{[2-hydroxy-4-(4-chlorobenzyloxy)]phenylmethylene}-1H-benzo[d]imidazole-6-formhydrazide N'-{[2-hydroxy-3-(1-methyl-2-allyl)]phenylmethylene}-1H-benzo[d]imidazole-6-formhydrazide N'-[(2-hydroxy)phenylmethylene]-1H-benzo[d]imidazole-6-formhydrazide N'-{[2-hydroxy-5-(4-chlorobenzyloxy)]phenylmethylene}-1H-benzo[d]imidazole-6-formhydrazide N'-[(2-hydroxy-4-benzyloxy)phenylmethylene]-1H-benzo[d]imidazole-6-formhydrazide N'-[(6-hydroxy-3,4-dioxomethylenephenyl)methylene]-1H-benzo[d]imidazole-2-acethydrazide N'-[(1-allyl-2,4,6-pyrimidinetrione-5-yl)methylene]-1H-benzo[d]imidazole-6-formhydrazide N'-[(2-hydroxy-4-chloro)phenylmethylene]-1H-benzo[d]imidazole-2-acethydrazide N'-[(2-hydroxy-5-isopropyl)phenylmethylene]-1H-benzo[d]imidazole-2-acethydrazide N'-[(2-hydroxy-5-fluoro)phenylmethylene]-1H-benzo[d]imidazole-6-formhydrazide N'-[(2-hydroxy-5-methoxy)phenylmethylene]-1H-benzo[d]imidazole-2-acethydrazide N'-{[6-hydroxy-5-propenyl-(2,3-dioxomethylene)phenyl]methylene}-1H-benzo[d]imidazole-2-acethydrazide N'-[(2-hydroxy-5-tert-butyl)phenylmethylene]-1H-benzo[d]imidazole-6-formhydrazide N'-[(2-hydroxy-3-allyl)phenylmethylene]-1H-benzo[d]imidazole-2-acethydrazide N'-[(1-hydroxy-2-naphthyl)methylene]-1H-benzo[d]imidazole-2-acethydrazide N'-{[2-hydroxy-5-methoxy-3-(3-methyl-2-butenyl)]phenylmethylene}-1H-benzo[d]imidazole-2-acethydrazide N'-[(2-hydroxy-3-allyl-5-tert-butyl)phenylmethylene]-1H-benzo[d]imidazole-2-acethydrazide N'-[(1-hydroxy-2-naphthyl)methylene]-1H-benzo[d]imidazole-6-formhydrazide N'-{[2-hydroxy-5-(3-chlorobenzyloxy)]phenylmethylene}-1H-benzo[d]imidazole-6-formhydrazide N'-[(2-hydroxy-3-allyl-5-isopropyl)phenylmethylene]-1H-benzo[d]imidazole-6-formhydrazide N'-[(2-hydroxy-5-trifluoromethoxy)phenylmethylene]-2-pyridin-4-yl-1H-benzo[d]imidazole-6-formhydrazide N'-[(2,3,4-trihydroxy)phenylmethylene]-1H-benzo[d]imidazole-2-acethydrazide N'-[(2-hydroxy-5-bromo)phenylmethylene]-1H-benzo[d]imidazole-2-acethydrazide N'-[(2-hydroxy-5-chloro)phenylmethylene]-1H-benzo[d] imidazole-6-formhydrazide N'-[(2-hydroxy-5-fluoro)phenylmethylene]-1H-benzo[d] imidazole-2-acethydrazide N'-[(2-hydroxy-4-fluoro)phenylmethylene]-1H-benzo[d] imidazole-2-acethydrazide N'-[(2-hydroxy-5-acetyl)phenylmethylene]-1H-benzo[d] imidazole-2-acethydrazide N'-[(2-hydroxy-4-fluoro-5-bromo)phenylmethylene]-1H-benzo[d]imidazole-2-acethydrazide N-[(2-hydroxy-5-cyano)phenylmethylene]-1H-benzo[d] imidazole-2-acethydrazide, and geometrical isomers, pharmaceutically acceptable salts, hydrates, solvates or prodrug thereof.

The most preferable particular compounds of instant invention are as follows:

N'-[(2-hydroxy-3,5-di-tert-butyl)phenylmethylene]-1H-benzo[d]imidazole-6-formhydrazide N'-[(2-hydroxy-3-allyl)phenylmethylene]-1H-benzo[d]imidazole-6-formhydrazide N'-[(2-hydroxy-4-methyl)phenylmethylene]-1H-benzo[d] imidazole-6-formhydrazide N'-[(2-hydroxy-1-naphthyl)methylene]-1H-benzo[d]imidazole-6-formhydrazide N'-{2-hydroxy-4-[2-(3,4-dioxomethylenebenzyl)thiazol-4-yl-methoxy]phenylmethylene}-1H-benzo[d]imidazole-6-formhydrazide N'-[(2-hydroxy-3,4,6-trimethyl)phenylmethylene]-1H-benzo[d]imidazole-2-acethydrazide N'-[(2-hydroxy-5-benzyloxy)phenylmethylene]-1H-benzo [d]imidazole-2-acethydrazide N'-{[2-hydroxy-4-(4-chlorobenzyloxy)]phenylmethylene}-1H-benzo[d]imidazole-6-formhydrazide N'-{[2-hydroxy-3-(1-methyl-2-allyl)]phenylmethylene}-1H-benzo[d]imidazole-6-formhydrazide and geometrical isomers, pharmaceutically acceptable salts, hydrates, solvates or prodrug thereof.

The term "pharmaceutically acceptable salt(s)" as used herein refer to a pharmaceutically acceptable salt formed by the compound of present invention reacted with acid. The acid includes inorganic or organic acids, and those salts formed by using the following acids are especially preferable: hydrochloric acid, oxalic acid, maleic acid, fumaric acid, citric acid, tartaric acid, malic acid, isethionic acid, methanesulfonic acid, ethanesulfonic acid, hydrobromic acid, sulfuric acid, phosphoric acid, acetic acid, propionic acid, lactic acid, trifluoroacetic acid, benzoic acid or paratoluenesulfonic acid.

In addition, the present invention includes the prodrugs of the derivatives of present invention. According to present invention, the prodrugs are the derivatives of general formula I, and the prodrugs have low biological activity or even have no biological activity, but which can be converted to a corresponding biologically-active form (e.g. by metabolism, solvolysis or other ways) under physiological conditions upon administration.

Unless indicated otherwise, the term "halogen" refers to fluorine, chlorine, bromine or iodine atom; "alkyl" refers to a straight or branched alkyl; "alkylene" refers to a straight or branched alkylene; "cycloalkyl" refers to substituted or unsubstituted cycloalkyl; heteroaryl comprises one or more heteroatoms selected from O, N and S, and may be one or more rings, and the ring system is aromatic and can be exemplified by imidazolyl, pyridinyl, pyrimidinyl, (1,2,3)- and (1,2,4)-triazolyl, pyrazinyl, tetrazolyl, furanyl, thiophenyl, isoxazolyl, oxazolyl, pyrazolyl, pyrrolyl, thiazolyl, benzoimidazolyl, pyridinoimidazolyl, benzothiophenyl, benzothiazolyl, indolyl, quinolinyl, pyridinopyrimidinyl and the like.

The present invention further relates to a pharmaceutical composition, comprising substituted hydrazide compounds as shown by general formula I, and geometrical isomers, pharmaceutically acceptable salts, hydrates, solvates or prodrug thereof as active ingredient, and pharmaceutically acceptable excipients if necessary. The pharmaceutically acceptable excipients refer to any diluents, adjuvants and/carrier that can be usable in pharmaceutical field.

The pharmaceutical composition of present invention could be prepared into various formulations comprising several excipients commonly used in the pharmaceutical art, for example, oral formulation (such as tablet, capsule, solution or suspension); injectable formulation (such as injectable solution or suspension, or injectable dry powder which is ready for use before injection by adding water for injection); and topical formulation (such as ointment or solution).

The carrier useful for the pharmaceutical composition of present invention is those commonly used in the pharmaceutical field, including adhesive, lubricant, disintegrating agent, cosolvent, diluents, stabilizer, suspending agent, pigment, flavoring agent and the like for oral formulation; preservative agent, solubilizer, stabilizer and the like for injectable formulation; and substrate, diluents, lubricant, preservative agent and the like for topical formulation. The pharmaceutical formulation may be administrated by oral or parenteral pathway (e.g., intravenous, subcutaneous, intraperitoneal or topical), and could be prepared into enteric coated tablet in case some medicines are unstable under the conditions of stomach.

We have found the compounds of present invention have an inhibitory effect on hyperplasia in vitro, including an inhibitory activity on tumor cell growth. Hence, the compounds can be useful for the preparation of medicaments for treating and/or preventing proliferative diseases, in particular breast, lung, colon, rectal, stomach, prostate, bladder, pancreas and ovarian cancers. It is also expected the compounds of the invention could be useful for the treatment of other proliferative diseases such as psoriasis, benign prostate hypertrophy, atherosclerosis and restenosis. Moreover, it is expected the substituted hydrazide compounds of the invention will possess an activity against leukemia, malignant lymphoma and solid tumors, for example cancer and sarcoma in tissues such as liver, kidney, prostate and pancreas.

The compounds of the invention can be useful as active ingredient for the preparation of medicaments for treating and/or preventing various cancers. The present invention further provides a method for treating and/or preventing above disease, comprising: administrating an effective amount of derivatives according to present invention to a patient suffering from or susceptible to such a disease. The clinic dosage of the substituted hydrazide compounds of general formula I for the patient will vary depending on the subject to be treated, the particular administration route, the severity of disease to be treated and the like, and optimal dosage shall be determined by physician responsible for the particular patient.

The active compound of the present invention may be used as a single anticancer medicament, or alternatively used in combination with one or more other antitumor medicament. Such a combined therapy can be achieved by administrating respective therapeutic components simultaneously, subsequently or separately.

The following Examples and Preparation Examples are provided to further illustrate and exemplify the compounds of the invention and preparation methods thereof. It shall not be understood that the following Examples and Preparation are intended to limit the scope of the invention in any way.

The following Scheme A illustrates the preparation of the compounds of general formula I of the present invention, wherein all starting materials can be prepared by the methods depicted in the Schemes or the methods well known to one of ordinary skill in the organic chemistry art, or are commercially available. All of the final compounds of the present invention are prepared by the methods depicted in the Schemes or similar methods, and these methods are well known to one of ordinary skill in the organic chemistry art. All variable factors as involved in these Schemes are defined as follows or defined as in claims.

In Scheme A, the compound of general formula I according to the invention (Ar, R and n) is defined as in Summary of the Invention. The compound II is reacted with hydrazine hydrate to obtain the compound III, which in turn is subjected to a condensation reaction with aldehyde IV having various substituents so as to obtain the compound represented by the general formula I.

Scheme A The synthesis route of compound of general formula I

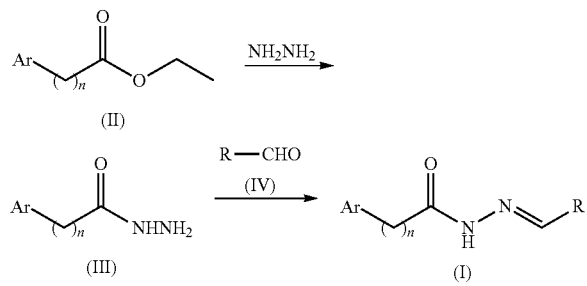

When Ar is

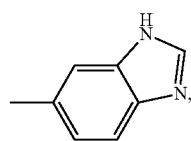

n=0, $R_1$ is hydrogen, or $R_1$ is a 5-10 membered heteroaryl substituted at 2-position of benzoimidazole ring, then the starting material II is prepared according to the method as depicted by Scheme II-1: firstly subjecting an esterification reaction by reacting 3,4-diaminobenzoic acid as starting material and ethanol, then a condensation cyclization reaction with a substituted formic acid, so as to give rise to 2-substituted benzo[d]imidazole-6-carboxylic acid ethyl ester (II-a).

Scheme II-1

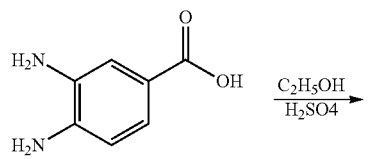

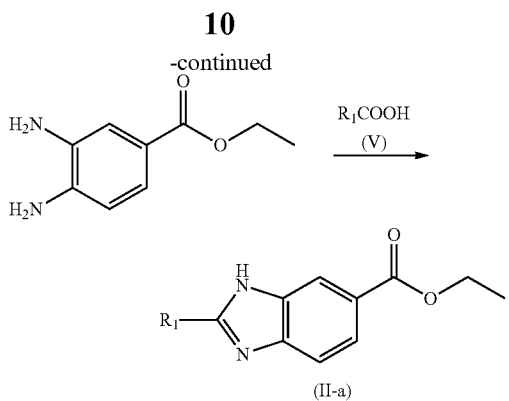

When Ar is

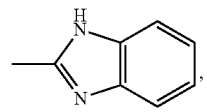

$R_1$ is hydrogen or arylC$_1$-C$_4$alkoxyl, then the starting material II is prepared according to the method as depicted by Scheme II-2: subjecting a condensation cyclization reaction by reacting o-phenylendiamine having a $R_1$ substitutent as starting material and 4-ethoxy-4-iminobutyric acid ethyl ester, so as to obtain substituted 1H-benzo[d]imidazole-2-acetic acid ethyl ester (II-b). The compound represented by starting material VI can be prepared by methods well known to one of ordinary skill in the organic chemistry field or alternatively can be commercially available.

Scheme II-2

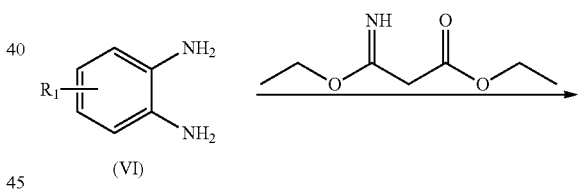

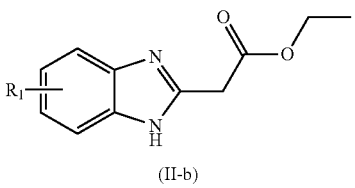

EMBODIMENTS

The following Examples aim to illustrate rather than limit the scope of the invention. The nuclear magnetic resonance hydrogen spectrum (HNMR) of the produced compounds of the invention was determined by Bruker ARX-300, and mass spectrum (MS) was determined by Agilent 1100 LC/MSD; all reagents were analytically pure or chemically pure.

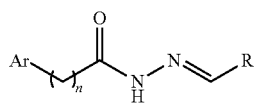

| Examples | Ar | R | n | Salt |
|---|---|---|---|---|
| 1 | 1H-benzimidazol-6-yl | 3,5-di-tert-butyl-2-hydroxy-phenyl (with methyl) | 0 | HCl |
| 2 | 1H-benzimidazol-6-yl | 2-hydroxy-5-methylphenyl | 0 | HCl |
| 3 | 1H-benzimidazol-6-yl | 2-hydroxy-1-naphthyl | 0 | HCl |
| 4 | 1H-benzimidazol-6-yl | 3-allyl-2-hydroxy-6-methylphenyl | 0 | HCl |
| 5 | 1H-benzimidazol-6-yl | substituted phenoxy-methyl-thiazole-benzodioxole | 0 | HCl |
| 6 | 1H-benzimidazol-6-yl | 2-hydroxy-3,4,6-trimethylphenyl (with CH₃ groups) | 0 | HCl |
| 7 | 1H-benzimidazol-6-yl | 2-hydroxy-5-methylphenyl | 0 | HCl |

-continued

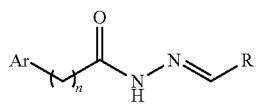

| Examples | Ar | R | n | Salt |
|---|---|---|---|---|
| 8 | 1H-benzimidazol-6-yl | 3-isopropyl-6-methyl-2-hydroxyphenyl (with CH₃) | 0 | HCl |
| 9 | 1H-benzimidazol-6-yl | 4-methyl-3-hydroxy-phenyl with 4-chlorobenzyloxy | 0 | HCl |
| 10 | 1H-benzimidazol-6-yl | 3-methyl-2-hydroxy-phenyl with but-3-en-2-yl | 0 | HCl |
| 11 | 1H-benzimidazol-6-yl | 2-hydroxy-phenyl | 0 | HCl |
| 12 | 1H-benzimidazol-6-yl | 3-methyl-4-hydroxy-phenyl with 4-chlorobenzyloxy | 0 | HCl |
| 13 | 1H-benzimidazol-6-yl | 4-methyl-3-hydroxy-phenyl with benzyloxy | 0 | HCl |
| 14 | 1H-benzimidazol-6-yl | 1-allyl-5-methyl-barbiturate | 0 | HCl |

-continued

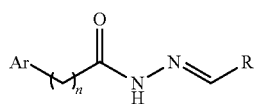

| Examples | Ar | R | n | Salt |
|---|---|---|---|---|
| 15 | 6-methyl-1H-benzimidazole | 4-fluoro-2-methylphenol | 0 | HCl |
| 16 | 6-methyl-1H-benzimidazole | 4-tert-butyl-2-methylphenol | 0 | HCl |
| 17 | 6-methyl-1H-benzimidazole | 1-hydroxy-2-methylnaphthalene | 0 | HCl |
| 18 | 6-methyl-1H-benzimidazole | 4-(3-chlorobenzyloxy)-2-methylphenol | 0 | HCl |
| 19 | 6-methyl-1H-benzimidazole | 2-allyl-4-isopropyl-6-methylphenol | 0 | HCl |
| 20 | 6-methyl-1H-benzimidazole | 4-chloro-2-methylphenol | 0 | HCl |
| 21 | 2-(pyridin-4-yl)-6-methyl-1H-benzimidazole | 2-methyl-4-(trifluoromethoxy)phenol | 0 | HCl |

-continued
| Examples | Ar | R | n | Salt |
|---|---|---|---|---|
| 22 | 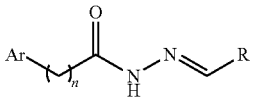 | 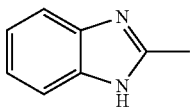 | 1 | HCl |
| 23 | 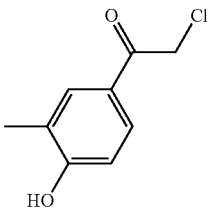 | 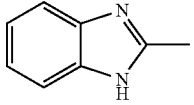 | 1 | HCl |
| 24 | 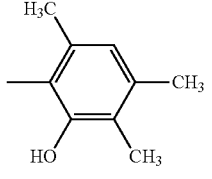 | 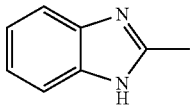 | 1 | HCl |
| 25 | 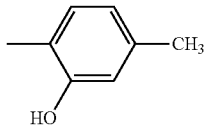 | 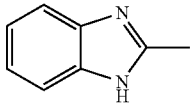 | 1 | HCl |
| 26 | 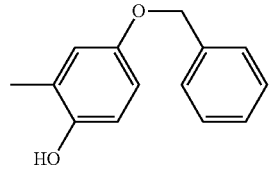 | 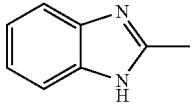 | 1 | HCl |
| 27 | 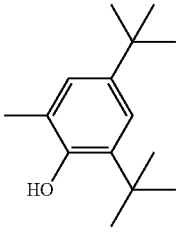 | 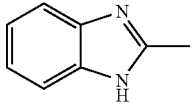 | 1 | HCl |
| 28 | 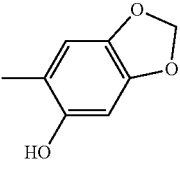 | 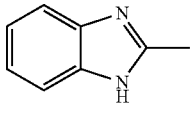 | 1 | HCl |
| 29 | 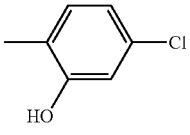 | 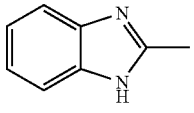 | 1 | HCl |

-continued

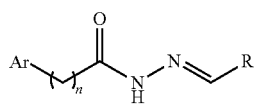

| Examples | Ar | R | n | Salt |
|---|---|---|---|---|
| 30 | 2-benzimidazolyl | 4-hydroxy-3-methyl-phenyl with OCH₃ | 1 | HCl |
| 31 | 2-benzimidazolyl | 2-hydroxy-4-fluoro-6-methyl-phenyl | 1 | HCl |
| 32 | 2-benzimidazolyl | methylenedioxy-hydroxy-propenyl-phenyl | 1 | HCl |
| 33 | 2-benzimidazolyl | 2-hydroxy-3-methyl-6-allyl-phenyl | 1 | HCl |
| 34 | 2-benzimidazolyl | 1-hydroxy-2-methyl-naphthyl | 1 | HCl |
| 35 | 2-benzimidazolyl | OCH₃, methyl, hydroxy, prenyl-phenyl | 1 | HCl |
| 36 | 2-benzimidazolyl | t-butyl, methyl, hydroxy, allyl-phenyl | 1 | HCl |
| 37 | 2-benzimidazolyl | 2,3-dihydroxy-4-hydroxy-6-methyl-phenyl | 1 | HCl |

-continued $$\text{Ar} \overset{\displaystyle O}{\underset{n}{\frown}} \underset{H}{N} \diagdown N \diagup \diagdown R$$

| Examples | Ar | R | n | Salt |
|---|---|---|---|---|
| 38 | 2-methyl-1H-benzo[d]imidazol-5-yl | 4-bromo-2-methyl-phenol (3-position linkage) | 1 | HCl |
| 39 | 2-methyl-1H-benzo[d]imidazol-5-yl | 4-fluoro-2-methyl-phenol (3-position linkage) | 1 | HCl |
| 40 | 2-methyl-1H-benzo[d]imidazol-5-yl | 4-acetyl-2-methyl-phenol (3-position linkage) | 1 | HCl |
| 41 | 2-methyl-1H-benzo[d]imidazol-5-yl | 4-bromo-5-fluoro-2-methyl-phenol | 1 | HCl |
| 42 | 2-methyl-1H-benzo[d]imidazol-5-yl | 4-cyano-2-methyl-phenol (3-position linkage) | 1 | HCl |

Example 1

N'-[(2-hydroxy-3,5-di-tert-butyl)phenylmethylene]-1H-benzo[d]imidazole-6-formhydrazide hydrochloride

Step A: Preparation of 3,4-diaminobenzoic acid ethyl ester 76 g of 3,4-diaminobenzoic acid (0.5 mol) and 300 mL anhydrous ethyl alcohol were added to a three-necked bottle, to which 6 mL concentrated sulphuric acid was added slowly under stirring at room temperature. After refluxing for 3 h, the reaction was completed. After concentration under reduced pressure, the residual solution was poured into ice water. The resulting mixture was adjusted to pH 7 with saturated sodium carbonate aqueous solution. After sucking filtration and drying, 81.5 g solid was obtained. Yield: 90.4%. MS: 181(M+1).

Step B: Preparation of 1H-benzo[d]imidazole-6-carboxylic acid ethyl ester 40 g of 3,4-diaminobenzoic acid ethyl ester (0.22 mol) and 200 mL formic acid were added to a three-necked bottle. After refluxing for 7 h, the reaction was completed. After concentration under reduced pressure, the ice water was poured into the residual solution. The resulting mixture was adjusted to pH 7 with sodium hydroxide. After sucking filtration, the filtrate was extracted with dichloromethane thrice, dried with anhydrous sodium sulfate, and decolored with active charcoal. Then the solution was concentrated under reduced pressure to get a white solid (29.6 g). Yield: 70.2%. MS: 191 (M+1)

Step C: Preparation of 1H-benzo[d]imidazole-6-formhydrazide 30 g of 1H-benzo[d]imidazole-6-carboxylic acid ethyl ester (0.16 mol) and 150 mL anhydrous ethyl alcohol were added to a three-necked bottle, to which 50 mL of 80% hydrazine hydrate was added. After refluxing for 4 h, the ethyl alcohol was evaporated under reduced pressure and water was added to the residual solution to isolate a solid. After sucking filtration and drying, 24.9 g solid was obtained. Yield: 88%. MS: 177 (M+1).

Step D: Preparation of N'-[(2-hydroxy-3,5-di-tert-butyl)phenylmethylene]-1H-benzo[d]imidazole-6-formhydrazide hydrochloride 0.5 g 1H-benzo[d]imidazole-6-formhydrazide (28 mmol), 0.66 g (28 mmol) 2-hydroxy-3,5-di-tert-butyl benzaldehyde and 20 mL anhydrous ethyl alcohol were added to a three-necked bottle. After refluxing for 6 h, a white solid was isolated. The mixture was cooled to room temperature and subjected to sucked filtration. The filter cake was washed with ethanol and dried to obtain an off-white powder. The above solid was added to 20 mL ethanol, to which an HCl ethanol solution was added dropwise with stirring at room temperature to adjust pH to 1~2. The solid was dissolved and agitation continued for 0.5 h to isolate a solid. After sucked filtration, washing with ethanol and drying, the compound of Example 1 was obtained (0.30 g). Yield: 25%. MS: 393(M+1);
$^1$H-NMR (DMSO-$d_6$) δ (ppm): 1.30 (s,9H), 1.43 (s,1H), 7.22 (s,1H), 7.31 (s,1H), 7.75 (d,1H), 7.86 (d,1H), 8.35 (s,1H), 8.40 (s,1H), 12.22 (s,1H), 12.38 (s,1H).

According to the method of Example 1, the compounds of Examples 2-21 were produced by selecting suitable material and reagents, respectively. When a specific reaction material is mentioned, it shall be understood that one skilled technologist in the field could select a suitable material and reagent according to the requirement of Example.

Example 2

N'-[(2-hydroxy-4-methyl)phenylmethylene]-1H-benzo[d]imidazole-6-formhydrazide hydrochloride MS: 295(M+1);
$^1$H-NMR (DMSO-$d_6$) δ (ppm): 2.29 (s,3H), 6.75 (s,1H), 6.77 (s,1H), 7.40 (d,1H), 7.71 (d,1H), 7.83 (d,1H), 8.26 (s,1H), 8.40 (s,1H), 8.61 (s,1H), 11.43 (s,1H), 12.08 (s,1H).

Example 3

N'-[(2-hydroxy-1-naphthyl)methylene]-1H-benzo[d]imidazole-6-formhydrazide hydrochloride MS: 331(M+1).
$^1$H-NMR (DMSO-$d_6$) δ (ppm): 2.08 (s,2H), 7.40 (d,1H), 7.44 (t,1H), 7.63 (t,1H), 7.77 (d,1H), 7.91 (m,4H), 8.20 (d,1H), 8.33 (s,1H), 8.47 (s,1H), 9.53 (s,1H), 12.23 (s,1H).

Example 4

N'-[(2-hydroxy-3-allyl)phenylmethylene]-1H-benzo[d]imidazole-6-formhydrazide hydrochloride Step E: Preparation of allyloxybenzene 94 g phenol (1 mol), 155 g anhydrous potassium carbonate (1.2 mol) and 300 mL acetone were added to a three-necked bottle, and stirred at 50° C. for 10 minutes. 107 g 3-bromopropylene (0.9 mol) was added dropwise, then the mixture was refluxed for 2 hours. After acetone was evaporated under reduced pressure, water was added to the residual solution and a solid was isolated. After sucked filtration, 108 g solid was obtained. Yield: 90.1%. MS: 135 (M+1).

Step F: Preparation of 2-allylphenol 27 g allyloxybenzene (0.2 mol) was added to a three-necked bottle. After temperature was raised to 180° C., all solid was melt-dissolved, maintaining this temperature for 2 hours. And then, the reaction solution was cooled to room temperature, added to 150 mL of 4% aqueous NaOH solution, and washed with ethyl acetate thrice. The aqueous layer was added with 10% aqueous HCl solution at room temperature to reach a pH of 4. A solid was isolated, which was sucked filtration, washed with water, and dried to obtain an off-white solid (17.8 g). Yield: 66%, MS: 135 (M+1).

Step G: Preparation of 3-allyl-2-hydroxy benzaldehyde 13.5 g 2-allylphenol (0.1 mol) and 100 mL acetonitrile were added to a three-necked bottle, to which 6.5 g paraformaldehyde, 22 g anhydrous magnesium chloride (0.39 mol) and triethylamine (0.02 mol) were added in this order with stirring at room temperature. After refluxing for 4 hours, the reaction solution was poured into ice water, which was adjusted with aqueous HCl solution to a pH of 5. After extraction with ethyl acetate twice, drying with anhydrous sodium sulfate and concentration under reduced pressure, 11 g solid was obtained. Yield: 68%, MS: 163 (M+1).

According to the methods depicted in steps E-F in Example 4, substituted benzaldehydes that were used in the preparation of Examples 4, 10, 19, 32, 33, 35, 36, 47, 48, 50, 51, 56, 57, 59 and 61 were prepared by selecting suitable starting materials and reagents, respectively. When a specific reaction material is mentioned, it shall be understood that one skilled technologist in the field could select a suitable material and reagent according to the requirement of Example.

According to the methods of Example 1, the compound of Example 4 (0.26 g) was produced. Yield: 29%, MS: 321 (M+1).

Example 5

N'-{2-hydroxy-4-[2-(3,4-dioxomethylenebenzyl)thiazol-4-ylmethoxy]phenylmethylene}-1H-benzo[d]imidazole-6-formhydrazide hydrochloride Step H: Preparation of 2-(3,4-dioxomethylenebenzyl)ethylthioamide 80 g homopiperonylonitrile (0.5 mol) was dissolved in 400 ml DMF solvent, to which 48 g anhydrous magnesium chloride (0.5 mol) and 56 g sodium hydrosulphide (1 mol) were added in this order. After reaction at room temperature for 1 h, standing, sucking filtration, washing with water and drying, 87.7 g yellow solid was obtained. Yield: 89.9%, MS: 196 (M+1).

Step I: Preparation of 2-[(3,4-dioxomethylenebenzyl)methyl]-4-(chloromethyl)thiazole 19.5 g 2-(3,4-dioxomethylenebenzyl)ethylthioamide (0.1 mol) was dissolved in 100 mL DMF, to which 12.6 g 1,3-dichloroacetone (0.1 mol) was added at room temperature. The reaction solution was heated at 60° C. for 3 hours, and then poured into ice water to isolate a solid. After sucking filtration and drying, 20.8 g off-white solid was obtained. Yield: 78%, MS: 268 (M+1).

Step J: Preparation of 2-hydroxy-4-{[2-(3,4-dioxomethylenebenzyl)methyl]thiazol-4-ylmethoxy}benzaldehyde 7.6 g 2,4-dihydroxy benzaldehyde (0.055 mol) was added to 100 mL DMF, to which 7.6 g anhydrous potassium carbonate (0.055 mol) was then added. After refluxing for 30 minutes, 13.5 g 2-[(3,4-dioxomethylenebenzyl)methyl]-4-(chloromethyl)thiazole (0.05 mol) was added and refluxing continued for 4 hours. The reaction solution was added to ice water and a solid was isolated. After sucking filtration and drying, a yellow solid was obtained (16.6 g). Yield: 90%, MS: 370 (M+1).

0.55 g compound of Example 5 was produced according to methods of Example 1. Yield: 37%, MS: 528(M+1).

Example 6

N'-[(2-hydroxy-3,4,6-trimethyl)phenylmethylene]-1H-benzo[d]imidazole-6-formhydrazide hydrochloride

MS: 323(M+1).

Example 7

N'-[(2-hydroxy-5-methyl)phenylmethylene]-1H-benzo[d]imidazole-6-formhydrazide hydrochloride

MS: 295(M+1).

Example 8

N'-[(2-hydroxy-3-methyl-6-isopropyl)phenylmethylene]-1H-benzo[d]imidazole-6-formhydrazide hydrochloride MS: 337(M+1);
$^1$H-NMR (DMSO-$d_6$) δ (ppm): 1.25 (d,6H), 2.17 (s,3H), 3.27 (m,1H), 6.76 (d,1H), 7.16 (d,1H), 7.73 (d,1H), 7.86 (dd,1H), 8.29 (s,1H), 8.46 (s,1H), 9.08 (s,1H), 12.14 (s,1H), 12.76 (s,1H).

Example 9

N'-{[2-hydroxy-4-(4-chlorobenzyloxy)]phenylmethylene}-1H-benzo[d]imidazole-6-formhydrazide hydrochloride Step K: Preparation of 2-hydroxy-4-(4-chlorobenzyloxy)benzaldehyde 13.8 g 2,4-dimethoxybenzaldehyde (0.1 mol), 100 mL acetone, 20.7 g anhydrous potassium carbonate (0.15 mol) and 19 g 4-chlorochlorobenzyl (0.12 mol) were added sequentially to a three-necked bottle, and reacted under reflux for 6 hours. The reaction solution was poured into ice water and a solid was isolated. After sucking filtration, washing with water and a little amount of ethanol, and drying, an off-white solid was obtained (16.1 g). Yield: 61%, MS: 263 (M+1).

According to the methods depicted in step K in Example 9, substituted benzaldehydes that were used in the preparation of Examples 9, 12, 13, 18, 25, 43, 44, 52, 58, 62 and 63 were prepared by selecting suitable starting materials and reagents, respectively. When a specific reaction material is mentioned, it shall be understood that one skilled technologist in the field could select a suitable starting material and reagent according to the requirement of Example.

0.58 g compound of Example 9 was produced according to the method of Example 1.

MS: 421(M+1);
$^1$H-NMR (DMSO-$d_6$) δ (ppm): 5.15 (2H,s), 6.60 (2H,d), 7.48 (5H,m), 7.70 (1H,d), 7.83 (1H,d), 8.26 (1H,s), 8.42 (1H,s), 8.57 (1H,s), 11.79 (1H,s), 12.04 (1H,s).

Example 10

N'-{[2-hydroxy-3-(1-methyl-2-allyl)]phenylmethylene}-1H-benzo[d]imidazole-6-formhydrazide hydrochloride MS: 435(M+1);
$^1$H-NMR (DMSO-$d_6$) δ (ppm): 1.70 (3H,s), 3.36 (2H,s), 4.66 (1H,s), 4.77 (1H,s), 6.92 (1H,t), 7.19 (1H,d), 7.33 (1H,d), 8.00 (1H,d), 8.17 (1H,d), 8.50 (1H,s), 8.74 (1H,s), 9.61 (1H,s), 12.04 (1H,s), 12.73 (1H,s).

Example 11

N'-[(2-hydroxy)phenylmethylene]-1H-benzo[d]imidazole-6-formhydrazide hydrochloride MS: 281(M+1);
$^1$H-NMR (DMSO-$d_6$) δ (ppm): 9.17 (s, 1H), 8.71 (s, 1H), 8.39 (s, 1H), 8.05 (d, J=8.4 Hz, 1H), 7.89 (d, J=8.4 Hz, 1H), 7.57 (d, J=7.2 Hz, 1H), 7.34 (t, J=14.4 Hz, 1H), 1.32 (t, J=16.2 Hz, 2H).

Example 12

N'-{[2-hydroxy-5-(4-chlorobenzyloxy)]phenylmethylene}-1H-benzo[d]imidazole-6-formhydrazide hydrochloride MS: 421(M+1);
$^1$H-NMR (DMSO-d6) δ (ppm): 9.54 (s, 1H), 8.71 (s, 1H), 8.44 (s, 1H), 8.14 (d, J=8.7 Hz, 1H), 7.97 (d, J=8.4 Hz, 1H), 7.51 (m, J=21.6 Hz, 4H), 7.24 (d, J=2.7 Hz, 1H), 7.03 (m, J=11.7 Hz, 1H), 6.90 (d, J=9 Hz, 1H), 5.08 (s, 1H).

Example 13

N'-[(2-hydroxy-4-benzyloxy)phenylmethylene]-1H-benzo[d]imidazole-6-formhydrazide hydrochloride

MS: 387(M+1).

Example 14

N'-[(1-allyl-2,4,6-pyrimidinetrione-5-yl)methylene]-1H-benzo[d]imidazole-6-formhydrazide

MS: 355(M+1).

Step L: Preparation of 1-allylpyrimidine-2,4,6(1H,3H,5H)-trione 9.2 g sodium thread (0.4 mol) was added to 300 mL anhydrous ethyl alcohol with stirring at room temperature. After the Na was dissolved completely, 30 mL diethyl malonate (0.2 mol) and 20 g allyl urea (0.2 mol) were added and refluxed for 5 hours. After the completion of reaction, sucking filtration was performed when the reaction solution was still hot. The filter cake was dissolved in 150 mL anhydrous ethyl alcohol and HCl was used to adjust the pH to 2~3. After sucking filtration, the filtrate was left to stand for crystallization. After sucking filtration again, washing with anhydrous ethyl alcohol and drying, a white solid (19.5 g) was obtained. Yield: 58%, MS: 169 (M+1).

Step M: Preparation of 1-allyl-5-[(dimethylamino) methylene]-pyrimidine-2,4,6-(1H,3H,5H)-trione 2 g 1-allylpyrimidine-2,4,6(1H,3H,5H)-trione (0.012 mol) and 16 ml DMF-DMA (0.12 mol) were added to a Eggplant shaped bottle, and reacted at room temperature for 5 minutes. After the completion of reaction, DMF-DMA was evaporated under reduced pressure to obtain a yellow solid with a dried weight of 2.2 g. Yield: 83%, MS: 224 (M+1).

0.46 g compound of Example 14 was produced according to the methods of Example 1. Yield: 47%, MS: 355 (M+1).

Example 15

N'-[(2-hydroxy-5-fluoro)phenylmethylene]-1H-benzo[d]imidazole-6-formhydrazide hydrochloride

MS: 299(M+1).

Example 16

N'-[(2-hydroxy-5-tert-butyl)phenylmethylene]-1H-benzo[d]imidazole-6-formhydrazide hydrochloride

MS: 337(M+1).

Example 17

N'-[(1-hydroxy-2-naphthyl)methylene]-1H-benzo[d]imidazole-6-formhydrazide hydrochloride

MS: 331(M+1).

Example 18

N'-{[2-hydroxy-5-(3-chlorobenzyloxy)]phenylmethylene}-1H-benzo[d]imidazole-6-formhydrazide hydrochloride

MS: 421(M+1).

Example 19

N'-[(2-hydroxy-3-allyl-5-isopropyl)phenylmethylene]-1H-benzo[d]imidazole-6-formhydrazide hydrochloride

MS: 363(M+1).

Example 20

N'-[(2-hydroxy-5-chloro)phenylmethylene]-1H-benzo[d]imidazole-6-formhydrazide hydrochloride

MS: 315(M+1).

Example 21

N'-[(2-hydroxy-5-trifluoromethoxy)phenylmethylene]-2-pyridin-4-yl-1H-benzo[d]imidazole-6-formhydrazide hydrochloride MS: 442(M+1);
$^1$H-NMR (DMSO-$d_6$) δ (ppm): 8.53 (d, J=12.9 Hz, 3H), 8.41 (d, J=14.4 Hz, 3H), 7.96 (d, J=6.9 Hz, 1H), 7.79 (s, 1H), 7.61 (s, 1H), 7.29 (d, J=7.8 Hz, 1H), 7.12 (d, J=9 Hz, 1H).

Example 22

N'-[(2-hydroxy-5-chloroacetyl)phenylmethylene]-1H-benzo[d]imidazole-2-acethydrazide hydrochloride Step N: Preparation of 3-ethoxy-3-imino Propionic Acid Ethyl Ester 113 g 2-cyanoacetic acid ethyl ester (1 mol) and 1000 mL anhydrous ethyl alcohol were added to a three-necked bottle, into which hydrogen chloride gas was bubbled with stirring at 0° C. After 4 hours, a lot of white solid were isolated and the reaction was stopped. After sucking filtration and drying, 60.0 g white solid was obtained. Yield: 91.6%, MS: 160 (M+1).

Step O: Preparation of 1H-benzo[d]imidazole-2-acetic Acid Ethyl Ester 54 g o-phenylenediamine (0.5 mol), 300 mL glacial acetic acid and 98 g 3-ethoxy-3-imino propionic acid ethyl ester (0.5 mol) were stirred at refluxing for 2 hours. After concentration under reduced pressure, the residual solution was poured into ice water and a solid was isolated. After sucking filtration, washing with water and a little amount of ethanol, and drying, 83 g off-white solid was obtained. Yield: 82%, MS: 205 (M+1).

Step P: Preparation of 1H-benzo[d]imidazole-2-acethydrazide 15 g 1H-benzo[d]imidazole-2-acetic acid ethyl ester (0.074 mol), 100 mL anhydrous ethyl alcohol and 37 mL of 80% hydrazine hydrate were added to a three-necked bottle and reacted under reflux for 4 hours. A white solid was isolated. After sucking filtration, the filter cake was washed with ethanol. After drying, 10.7 g white solid was obtained. Yield: 76%, MS: 191(M+1).

Step Q: Preparation of 5-(2-chloroacetyl)-2-hydroxy benzaldehyde 12.2 g salicylic aldehyde (0.1 mol) and 200 mL dry dichloromethane were added to a three-necked bottle, to which 133 g anhydrous aluminium trichloride (1 mol) was added in batches at 0° C., then 55.5 g chloroacetyl chloride solution in dichloromethane (0.5 mol) was slowly added dropwise. After refluxing for 48 hours, the reaction solution was poured into ice water, and saturated sodium carbonate aqueous solution was used to adjust the pH to 6~7. The separated dichloromethane layer was washed with water and saturated ammonium chloride solution each for three times, dried with anhydrous sodium sulfate, concentrated under reduced pressure to obtain an off-white solid (11 g). Yield: 56%, MS: 199(M+1).

0.26 g compound of Example 22 was produced according to the method of Example 1. Yield: 31.1%, MS: 371(M+1).

¹H-NMR (DMSO-d₆) δ (ppm): 8.59 (d, J=49.8, 1H), 8.36 (d, J=17.4 Hz, 1H), 7.96 (t, J=15.9 Hz, 1H), 7.85 (m, J=9.3 Hz, 2H), 7.57 (t, J=9 Hz, 2H), 7.09 (d, J=8.7 Hz, 1H), 5.13 (s, 2H), 4.78 (s, 1H), 4.38 (s, 1H).

According to the methods of Example 22, the compounds of Examples 23-42 were prepared by selecting suitable starting materials and reagents, respectively. When a specific reaction material is mentioned, it shall be understood that one skilled technologist in the field could select suitable materials and reagents according to the requirement of Examples.

Example 23

N'-[(2-hydroxy-3,4,6-trimethyl)phenylmethylene]-1H-benzo[d]imidazole-2-acethydrazide hydrochloride MS: 337(M+1);
¹H-NMR (DMSO-d₆) δ (ppm): 2.06(3H,s), 2.20 (3H,s), 2.33 (3H,s), 2.06 (2H,s), 6.60 (1H,s), 7.55 (2H,d), 7.83 (2H, d), 8.77 (1H,s), 12.12 (1H,s), 12.75 (1H,s).

Example 24

N'-[(2-hydroxy-4-methyl)phenylmethylene]-1H-benzo[d]imidazole-2-acethydrazide hydrochloride

MS: 308(M+1);

Example 25

N'-[(2-hydroxy-5-benzyloxy)phenylmethylene]-1H-benzo[d]imidazole-2-acethydrazide hydrochloride MS: 401(M+1);
¹H-NMR (DMSO-d₆) δ (ppm): 8.94 (d, J=132.9Hz 1H), 8.36 (m, J=163.8Hz, 2H), 7.81 (m, J=84.3 Hz, 2H), 7.47 (m, 7H), 7.02 (m, J=34.2 Hz, 1H), 6.87 (d, J=8.7 Hz, 1H), 5.07 (s, 2H), 3.82 (s, 2H), 4.73 (s, 2H).

Example 26

N'-[(2-hydroxy-3,5-di-tert-butyl)phenylmethylene]-1H-benzo[d]imidazole-2-acethydrazide hydrochloride MS: 307(M+1);
¹H-NMR (DMSO-d₆) δ (ppm): 1.28 (s,9H), 1.38 (s,9H), 4.40 (d,2H), 7.29 (s,1H), 7.31 (s,1H), 7.54 (m,2H), 7.81 (m,2H), 8.30 (s,1H), 8.46 (s,1H), 10.52 (s,1H), 12.00 (s,1H).

Example 27

N'-[(6-hydroxy-3,4-dioxomethylenephenyl)methylene]-1H-benzo[d]imidazole-2-acethydrazide hydrochloride

MS: 339(M+1).

Example 28

N'-[(2-hydroxy-4-chloro)phenylmethylene]-1H-benzo[d]imidazole-2-acethydrazide hydrochloride MS: 329(M+1);
¹H-NMR (DMSO-d₆) δ (ppm): 4.34 (s,1H), 4.71 (s,1H), 6.99 (m,2H), 7.54 (m,2H), 7.73 (d,1H), 7.82 (m,2H), 8.34 (s,1H), 8.49 (s,1H), 10.70 (s,1H), 11.96 (s,1H).

Example 29

N'-[(2-hydroxy-5-isopropyl)phenylmethylene]-1H-benzo[d]imidazole-2-acethydrazide hydrochloride

MS: 337(M+1).

Example 30

N'-[(2-hydroxy-5-methoxy)phenylmethylene]-1H-benzo[d]imidazole-2-acethydrazide hydrochloride

MS: 325(M+1).

Example 31

N'-[(2-hydroxy-4-fluoro)phenylmethylene]-1H-benzo[d]imidazole-2-acethydrazide hydrochloride

MS: 313(M+1).

Example 32

N'-{[6-hydroxy-5-propenyl-(2,3-dioxomethylene)phenyl]methylene}-1H-benzo[d]imidazole-2-acethydrazide hydrochloride MS: 379(M+1);
¹H-NMR (300 MHz, DMSO) δ: 8.44 (s, 1H), 7.89 (d, J=7.8Hz, 2H), 7.55 (d, J=12 Hz, 1H), 7.44 (t, J=17.7 Hz, 2H), 6.78 (d, J=3.9 Hz, 1H), 6.02 (s, 1H), 5.95 (m, J=27 Hz, 2H), 3.82 (d, 2H), 2.36 (d, 3H).

Example 33

N'-[(2-hydroxy-3-allyl)phenylmethylene]-1H-benzo[d]imidazole-2-acethydrazide hydrochloride

MS: 325(M+1).

Example 34

N'-[(1-hydroxy-2-naphthyl)methylene]-1H-benzo[d]imidazole-2-acethydrazide hydrochloride

MS: 345(M+1).

Example 35

N'-{[2-hydroxy-5-methoxy-3-(3-methyl-2-butenyl)]phenylmethylene}-1H-benzo[d]imidazole-2-acethydrazide hydrochloride

MS: 393(M+1).

Example 36

N'-[(2-hydroxy-3-allyl-5-tert-butyl)phenylmethylene]-1H-benzo[d]imidazole-2-acethydrazide hydrochloride

MS: 391(M+1);

$^1$H-NMR (DMSO-$d_6$) δ (ppm): 1.27 (s,9H), 3.37 (d,2H), 4.43 (d,2H), 4.7 (s,1H), 5.05 (t,1H), 7.24 (s,1H), 7.32 (s,1H), 7.53 (dd,2H), 7.84 (d,2H), 8.36 (s,1H), 8.49 (s,1H), 10.84 (s,1H).

Example 37

N'-[(2,3,4-trihydroxy)phenylmethylene]-1H-benzo[d]imidazole-2-acethydrazide hydrochloride

MS: 327(M+1).

Example 38

N'-[(2-hydroxy-5-bromo)phenylmethylene]-1H-benzo[d]imidazole-2-acethydrazide hydrochloride

MS: 373(M+1).

Example 39

N'-[(2-hydroxy-5-fluoro)phenylmethylene]-1H-benzo[d]imidazole-2-acethydrazide hydrochloride

MS: 313(M+1).

Example 40

N'-[(2-hydroxy-5-acetyl)phenylmethylene]-1H-benzo[d]imidazole-2-acethydrazide hydrochloride

MS: 337(M+1);

$^1$H-NMR (300 MHz, DMSO) δ: 8.58 (d, J=45.9, 1H), 8.33 (d, J=1.8 Hz, 1H), 7.92 (t, J=6.3 Hz, 1H), 7.85 (m, J=13.2 Hz, 2H), 7.56 (m, J=9.3 Hz, 2H), 7.05 (d, J=8.7 Hz, 1H), 4.76 (s, 2H), 2.53 (s, 3H).

Example 41

N'-[(2-hydroxy-4-fluoro-5-bromo)phenylmethylene]-1H-benzo[d]imidazole-2-acethydrazide hydrochloride

MS: 391(M+1).

Example 42

N'-[(2-hydroxy-5-cyano)phenylmethylene]-1H-benzo[d]imidazole-2-acethydrazide hydrochloride

MS: 320(M+1).

Example 43

Pharmacological Study of Products of the Invention

The substituted hydrazide compounds of above formula I of the invention were screened for antitumor activity in vitro.

Antitumor Activity Assay in vitro (1) Five cell strains, SK-N-SH (human neuroblastoma cell), NCI-H226 (human lung cancer cell), Bel7402 (human liver cancer cell), A549 (human non-small cell lung cancer), and MCF7 (human breast cancer cell), were thawed and stably passaged for two or three times, respectively, and then digested with trypsin solution (0.25%) so as to be removed from the bottom of culture flasks. The digested cell solution was poured into a centrifuge tube, to which culture media was added to stop the digestion. The centrifuge tube was centrifuged at 1300 r/min for 3 min, the supernatant was removed gently and then 5 mL culture media was added. The cells were pipetted and mixed homogeneously. 10 μL cell suspension was taken into a cell counting plate for counting, wherein the cell concentration was adjusted to $10^4$ cells/well. Each well of the 96-well plates, except for A1 well as blank control, contained 100 μL cell suspension. The 96-well plates were placed in an incubator and cultivated for 24 hours.

(2) 50 μL dimethyl sulfoxide was used to dissolve the test samples, and then a suitable amount of culture media was added so as to reach a final concentration of 2 mg/mL. Then the samples were diluted to 100, 20, 4, 0.8, 0.16 μg/mL in a 24-well plate, respectively. There were three wells for each concentration, wherein the cell growth in the surrounding two rows and columns was significantly influenced by environments and thus only taken as blank cell wells. The 96-well plates were placed in an incubator and cultivated for 72 hours.

(3) The culture media containing the compounds in the 96-well plates was discarded, and the cells were washed with phosphate buffered solution (PBS) twice. Each well was added with 100 μL MTT (tetrazole) (0.5 mg/mL), and then placed in an incubator to incubate for 4 hours, after which MTT solution was discarded and 100 μL dimethyl sulfoxide was added thereto. The reaction product of survival cells with MTT, i.e. formazan, was dissolved completely by oscillation on a magnetic oscillator, then placed into a microplate reader to measure the results, and the $IC_{50}$ values of compounds could be deduced by Bliss method. The control, N'-[(2-hydroxy-3-allyl)phenylmethylene]-2-(4-benzylpiperazin-1-yl) acethydrazide(PAC-1), was produced according to the method of patent WO2008/134474 A2.

The in vitro activity of the compounds against tumor cells was shown in Table 1.

TABLE 1

In vitro antitumor activity of Example compounds

| Example Nos. | $IC_{50}$ (μg/mL) | | | | |
|---|---|---|---|---|---|
| | SK | NCI-226 | Bel7402 | A549 | MCF7 |
| Example 1 | 0.08 | 0.07 | 0.56 | 0.4 | 0.8 |
| Example 2 | 2.1 | 1.0 | 2.4 | 1.9 | 1.8 |
| Example 3 | 3.0 | 1.1 | 2.5 | 0.7 | 1.2 |
| Example 4 | 1.3 | 0.2 | 1.3 | 2 | 3.3 |
| Example 5 | 3.3 | 2.4 | 2.9 | 11 | 3.8 |
| Example 6 | 1.8 | 1.7 | 2.6 | 3.1 | 3.2 |
| Example 7 | 3.2 | 2.7 | 5.4 | 12 | 1.9 |
| Example 8 | 3.0 | 1.0 | 2.4 | 1.5 | 1.7 |
| Example 9 | 0.2 | 0.5 | 1.5 | 0.9 | 0.6 |
| Example 10 | 1.1 | 1.0 | 3.3 | 1.2 | 3.8 |
| Example 11 | 2.7 | 2.3 | 3.2 | 10 | 2.3 |

TABLE 1-continued

In vitro antitumor activity of Example compounds

| Example Nos. | IC$_{50}$ (μg/mL) | | | | |
|---|---|---|---|---|---|
| | SK | NCI-226 | Bel7402 | A549 | MCF7 |
| Example 12 | 3.0 | 1.7 | 3.3 | 5.8 | 2.1 |
| Example 13 | 1.1 | 2.4 | 3.7 | 2.6 | 1.8 |
| Example 14 | 0.9 | 2.5 | 2.2 | 10 | 1.7 |
| Example 18 | 1.7 | 2.3 | 3.1 | 1.5 | 2.7 |
| Example 22 | 1.0 | 0.8 | 0.5 | 1.7 | 3.4 |
| Example 23 | 0.3 | 0.3 | 3.1 | 2.4 | 2.6 |
| Example 25 | 0.4 | 1.6 | 3.7 | 4.1 | 1.0 |
| PAC-1 | 4.3 | 1.7 | 3.8 | 1.9 | 2.6 |

As can be seen clearly from the above test results, the claimed compounds of general formula I possess a good in vitro antitumor activity and are better than the antitumor drug PAC-1.

The compounds of general formula I according to present invention may be administrated alone, but typically administrated in mixture with a pharmaceutically acceptable carrier. The selection of the pharmaceutically acceptable carrier depends on the desired administration route and standard pharmaceutical practice. The following various pharmaceutical formulations of the compounds, such as tablet, capsule, injection, aerosol, suppository, film, dripping pill, liniment for external use, and ointment, are used to illustrate the new application of these compounds in medicine field.

Example 44

Tablet 10 g compound (e.g., the compound of Example 1) containing the compound of claim 1 was mixed homogeneously with 20 g adjuvants and tabletted into 100 tablets by general compression method, 300 mg each tablet.

Example 45

Capsule 10 g compound (e.g., the compound of Example 1) containing the compound of claim 1 was mixed homogeneously with 20 g adjuvants according to the requirements of pharmaceutical capsules, and filled into empty capsules, 300 mg each capsule.

Example 46

Injection 10 g compound (e.g., the compound of Example 1) containing the compound of claim 1 was absorbed by activative charcoal by conventional pharmaceutical method, filtered through 0.65 μm microporous membrane and filled into nitrogen bottle to prepare water injection preparation, 2 mL each bottle, and 100 bottles in total.

Example 47

Aerosol 10 g compound (e.g., the compound of Example 1) containing the compound of claim 1 was dissolved with a suitable amount of propylene glycol, and added with distilled water and other adjuvants to get 500 mL clear solution.

Example 48

Suppository 10 g compound (e.g., the compound of Example 1) containing the compound of claim 1 was grinded and a suitable amount of glycerol was added and mixed homogeneously. Then melt glycerol gelatin was added and grinded homogeneously, and the mixture was poured into a mold coated with lubricant to produce 50 suppository particles.

Example 49

Film 10 g compound (e.g., the compound of Example 1) containing the compound of claim 1 was mixed and expanded with polyvinyl alcohol, pharmaceutically acceptable glycerol, water etc., and dissolved by heating. After filtration on an 80 mesh screen, the compound of Example 18 was added to the filtrate and dissolved therein by agitation. 100 films were produced by coater machine.

Example 50

Dripping Pill 10 g compound (e.g., the compound of Example 1) containing the compound of claim 1 was mixed homogeneously with 50 g substrate such as gelatin by heating and melting, then the mixture was dropped into a liquid paraffin at low temperature. 1000 pills of dripping pill were produced.

Example 51

Liniment for External Use 10 g compound (e.g., the compound of Example 1) containing the compound of claim 1 was mixed and ground with 2.5 g adjuvants such as emulsifier by conventional formulation methods, then 200 mL water was added to prepare the liniment for external use.

Example 52

Ointment 10 g compound (e.g., the compound of Example 1) containing the compound of claim 1 was ground and then mixed homogeneously with 500 g oleaginous base such as Vaseline.

Although the invention has been illustrated by above specific embodiments, any modification and equivalent variation are obvious to those skilled in the art and they fall into the scope of the invention.

The invention claimed is:
1. A compound selected from the group consisting of:
   N'-[(2-hydroxy-3,5-di-tert-butyl)phenylmethylene]-1H-benzo[d]imidazole-6-formhydrazide,
   N'-[(2-hydroxy-3-allyl)phenylmethylene]-1H-benzo[d]imidazole-6-formhydrazide,
   N'-[(2-hydroxy-4-methyl)phenylmethylene]-1H-benzo[d]imidazole-6-formhydrazide,
   N'-[(2-hydroxy-1-naphthyl)methylene]-1H-benzo[d]imidazole-6-formhydrazide,

N'-{2-hydroxy-4-[2-(3,4-dioxomethylenebenzyl)thiazol-4-yl-methoxy]phenylmethylene}-1H-benzo[d]imidazole-6-formhydrazide, N'-{[2-hydroxy-4-(4-chlorobenzyloxy)]phenylmethylene}-1H-benzo[d]imidazole-6-formhydrazide, and N'-{[2-hydroxy-3-(1-methyl-2-allyl)]phenylmethylene}-1H-benzo[d]imidazole-6-formhydrazide.

2. A pharmaceutical composition, comprising a compound or pharmaceutically acceptable salt thereof according to claim 1.

3. A method for the treatment of a cancer comprising administering a therapeutically effective amount of a compound according to claim 1 to a subject in need thereof, wherein the cancer is selected from the group consisting of neuroblastoma, lung cancer, liver cancer, non-small cell lung cancer and breast cancer.

* * * * *